United States Patent [19]

Mathew et al.

[11] 4,380,660
[45] Apr. 19, 1983

[54] PRODUCING ALKOXYSILANES AND ALKOXY-OXIMINOSILANES

[75] Inventors: Chempolil T. Mathew, Randolph; Harry E. Ulmer, Morristown, both of N.J.

[73] Assignee: Allied Corporation, Morris Township, Morris County, N.J.

[21] Appl. No.: 394,353

[22] Filed: Jul. 1, 1982

[51] Int. Cl.$^3$ ............................ C07F 7/10; C07F 7/18
[52] U.S. Cl. ..................................... 556/422; 556/471
[58] Field of Search ................................ 556/471, 422

[56] References Cited

U.S. PATENT DOCUMENTS

| | | | |
|---|---|---|---|
| 3,277,136 | 10/1966 | Thiesse | 556/471 |
| 3,448,136 | 6/1969 | Pande et al. | 556/422 X |
| 3,546,267 | 12/1970 | Ismail | 556/471 |
| 4,126,630 | 11/1978 | Müller et al. | 556/422 X |

FOREIGN PATENT DOCUMENTS 239144  3/1969  U.S.S.R. .............................. 556/422
494384  8/1976  U.S.S.R. .............................. 556/422

OTHER PUBLICATIONS

Chemical Abstracts, vol. 83:179292k.
Chemical Abstracts, vol. 75;89238c.
Chemical Abstracts, vol. 80:4671u.

Primary Examiner—Paul F. Shaver
Attorney, Agent, or Firm—Alan M. Doernberg; Gerhard H. Fuchs; Kenneth E. Stroup, Jr.

[57] ABSTRACT

A silicon halide such as methyl trichlorosilane is reacted with an alcohol such as isopropanol and an oxime such as methyl ethyl ketone oxime. Byproduct oxime hydrohalide is formed in all cases. With higher amounts of alcohol, alkoxysilane (e.g. methyl triisopropoxysilane) is the sole or major product. With lower amounts of alcohol, alkoxy-oxminosilanes (e.g. methyl diisopropoxy(methyl ethyl ketoximo)silane and methyl isopropoxy bis(methyl ethyl ketoximo)silane) are the major products.

20 Claims, 1 Drawing Figure

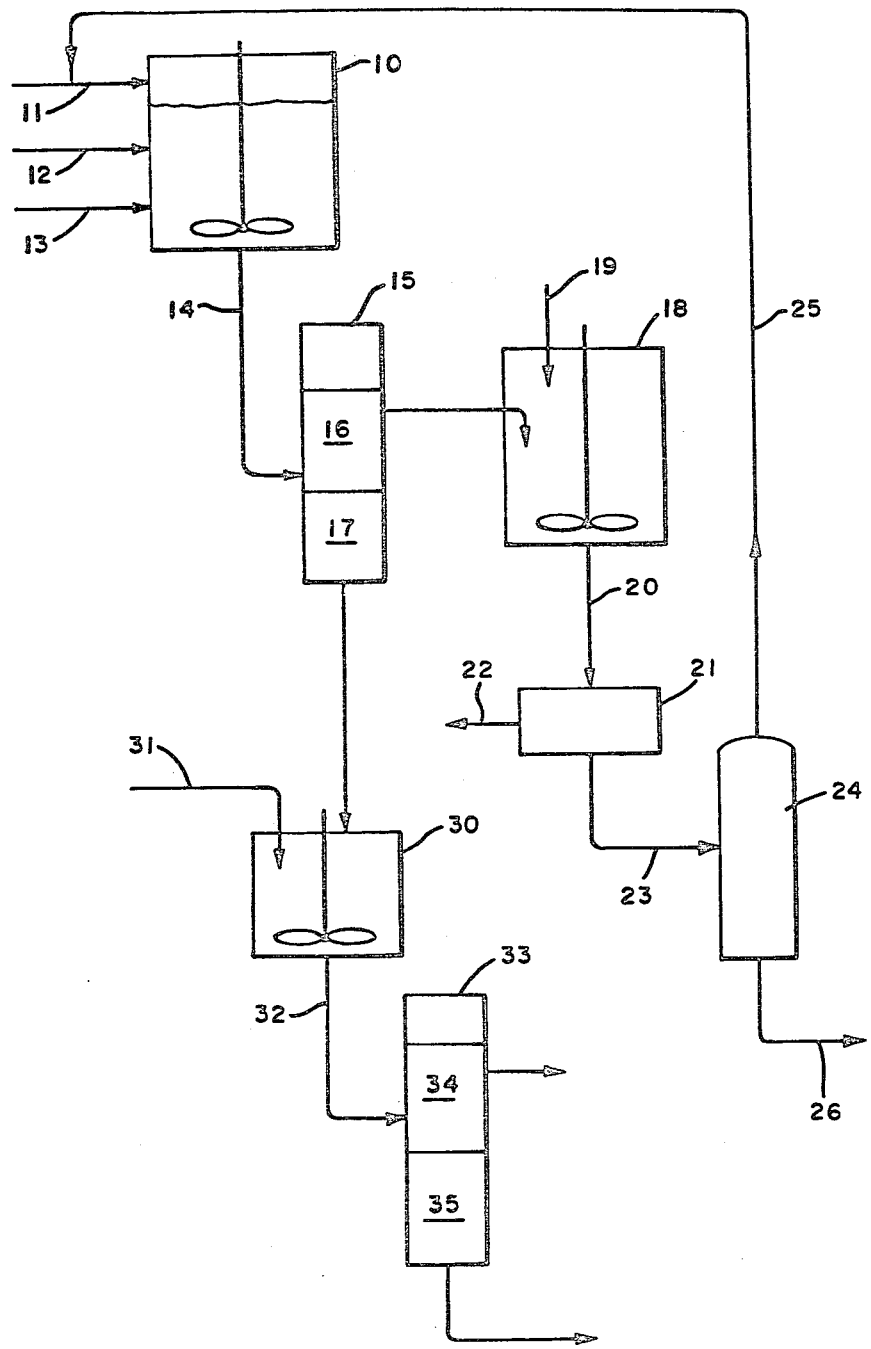

PRODUCING ALKOXYSILANES AND ALKOXY-OXIMINOSILANES

BACKGROUND OF THE INVENTION

The present invention relates to producing alkoxysilanes and alkoxy-oximinosilanes which are useful as initiators or room temperature vulcanizing agents in silicone rubber compounds.

Prior art processes for the production of alkoxysilanes have involved the reaction of silicon chlorides such as methyltrichlorosilane (MTCS) with alcohols, with strong bases such as pyridine or sodium metal used to neutralize the byproduct HCl and drive the reaction to completion. Similar processes have been disclosed for producing oximinosilanes, with an oxime substituted for the alcohol.

In Russian Author's Certificate No. 547,245 of G. V. Ryasin et al., (published May 22, 1981), a process is described in which an oxime acts as both reactant and acid acceptor, such that six moles of methyl ethyl ketoxime (MEKO) and one mole of MTCS produce one mole of methyl tris(methyl ethyl ketoximo) silane and three moles of MEKO hydrochloride. Our copending, commonly assigned U.S. application Ser. No. 331,694 (filed Dec. 17, 1981) discloses such a process in which the product is recovered without requiring a product distillation.

Oximinosilanes are superior in performance to alkoxysilanes as initiators for silicone rubbers because of more rapid hydrolysis. Alkoxysilanes have the advantage of cheaper raw materials cost. The advantages of both materials might be obtained by using some of each in a molding composition. A more desirable alternative would be to combine both functionalities on the same molecule. See German Offen No. 2,055,712 (1971) (Chem Abstr 75:89238c); 2,065,407 (1973) (Chem Abstr 80:4671u); and Japan No. 74:39,967 (1974) (Chem Abstr 83:179292k).

BRIEF DESCRIPTION OF THE INVENTION

It has been discovered that oximes are good acid acceptors for the reaction between alcohols and a silicon halide, allowing the alkoxysilane to be formed to the virtual exclusion of oximinosilane when the alcohol is present in sufficient amounts. It has also been discovered that, with less alcohol present than required to react all halogens, initiator products having a mixture of alkoxy and oximino groups are formed. Both reactions produce byproduct oxime hydrohalide which is readily separable from the organosilane product, which organosilane product can be recovered and purified by treatment with dry base.

Accordingly, the present invention includes a process for the production of an alkoxysilane which comprises:

(a) reacting a silicon halide of the formula $R_{4-n}SiX_n$, wherein n is an integer between 1 and 4, inclusive, and R is alkyl of 1-6 carbons, alkenyl of 2-6 carbons, cycloalkyl of 4-8 carbons, aryl, alkyl-substituted aryl, aralkyl or halosubstituted forms of any of these with an alcohol of the formula R'OH, with R' being alkyl of 1-24 carbons or aralkyl, in the presence of an oxime compound of the formula R"R"'C=NOH, with R" and R"' each being hydrogen or alkyl of 1-6 carbons or forming a halosubstituted, alkylsubstituted or unsubstituted cycloalkyl ring of 4-8 carbons and X is Cl, Br or I;

the molar ratio of alcohol to silicon halide being at least n:1 and the molar ratio of oxime to silicon halide being at least n:1; and (b) recovering the alkoxysilane of the formula $R_{4-n}Si(OR')_n$ as major product and the hydrohalide of said oxime as byproduct.

In addition, the present invention includes a process for the production of alkoxyoximinosilanes which comprises:

(a) reacting a silicon halide of the formula $R_{4-n}SiX_n$ where R is alkyl of 1-6 carbons, alkenyl of 2-6 carbons, cycloalkyl of 4-8 carbons, aryl, alkyl-substituted aryl, aralkyl or halosubstituted forms of any of these and n is an integer of 2-4 with an alcohol of the formula R'OH, where R' is alkyl of 1-24 carbons or aralkyl, and an oxime of the formula R"R"'C=NOH, with R" and R"' each being hydrogen or alkyl of 1-6 carbons or forming an unsubstituted, halosubstituted or alkyl-substituted cycloalkyl ring of 4-8 carbons and X is Cl, Br or I;

the molar ratio of alcohol to silicon halide being m:1, wherein m is at least about 0.1 n and less than n, and the molar ratio of oxime to silicon halide being at least (2n-m):1; and (b) recovering a product comprising at least one alkoxyoximinosilane of the formula $R_{4-n}Si(OR')_p(ON=CR"R"')_{n-p}$ where p is an integer of 1-3, but is at least one less than n, and the hydrohalide of said oxime as byproduct.

DETAILED DESCRIPTION OF THE INVENTION

The reactants in the present invention are the halosilane, the oxime compound and the alcohol. Suitable halosilanes (silicon halide such as silicon chlorides) may be represented by the formula $R_{4-n}SiX_n$. In this formula R may be alkyl of 1-6 carbons such as methyl, ethyl, propyl, isopropyl, butyl, pentyl, or hexyl; may be alkenyl of 2-6 carbons such as vinyl, 2-propenyl, 3-butenyl or 2-pentenyl; may be aryl such as phenyl; may be cycloalkyl such as cyclobutyl, cyclopentyl, cyclohexyl or cyclooctyl; may be alkyl-substituted aryl such as p-methylphenyl, p-ethylphenyl or p-tertbutylphenyl; may be aralkyl such as benzyl; or may be halosubstituted forms of any of these such as 3-chlorocyclohexyl, chloromethyl, p-chlorophenyl or p-bromophenyl. Furthermore, different R's on the same molecule may differ, as in methyl ethyl dichlorosilane. Preferred substituents R are methyl, ethyl, vinyl and phenyl; with methyl and vinyl being most preferred. In the above formula X may be Cl, Br or I, and is preferably Cl. Also in the above formula n may be 1, 2, 3 or 4, but is preferably 3 such that there is one R and three X's.

Representative silicon halides which may be reacted with oxime compounds in the present process of producing alkoxysilanes include methyl trichlorosilane, phenyl trichlorosilane, vinyl trichlorosilane, dimethyl dichlorosilane, trimethyl chlorosilane, methyl ethyl dichlorosilane, 2-chloroethyl trichlorosilane, silicon tetrchloride, diethyl dichlorosilane, dimethyl dibromosilane, triethyl chlorosilane, benzyl trichlorosilane, allyl trichlorosilane, trimethyl bromosilane, triphenyl silyl chloride and trimethyl silyl iodide. All of the above except the tree trimethylhalosilanes and triphenyl silyl chloride are also suitable for forming oximinoalkoxysilanes. Preferred are silicon halides wherein n is 3 and wherein R is alkyl (e.g. methyl and ethyl) or alkenyl (e.g. vinyl) or phenyl.

The oxime used in the present process may be any compound of the formula R"R'"C=NOH. In this formula R" and R'" may each be H or alkyl of 1-6 carbons, aryl, cycloalkyl, aralkyl; or any of these substituted by halo; or R" and R'" may together by $(CH_2)_m$ wherein m is an integer from 3 to 7; or R" and R'" may together be such a group substituted by alkyl or halogen. If R" or R'" or the two together are substituted by halogen, then the molecule should be one in which the halogen is not reactive (e.g. halogen on a tertiary carbon). Thus suitable oximes include formaldehyde oxime, 4-methylcyclohexanone oxime, 4-chlorocyclohexanone oxime, acetophenone oxime, benzophenone oxime, benzyl ethyl ketone oxime, cyclohexyl methyl ketone oxime and benzaldehyde oxime. Preferred oxime compounds include acetaldehyde oxime, acetone oxime, methyl ethyl ketone oxime, diethyl ketone oxime and cyclohexanone oxime; with methyl ethyl ketone oxime and acetone oxime being more preferred. Methyl ethyl ketone oxime is most preferred because of its use in many oximinosilane compounds used as room temperature vulcanizing agents for silicon polymers.

The alcohol R'OH used in the present invention may be primary, secondary or tertiary, may otherwise be branched or substituted and may be aralkyl, Examples include methanol, ethanol, n-propanol, isopropanol, isobutanol, t-butanol, isoamyl alcohol, hexanol, benzyl alcohol, decanol, hexadecanol, stearyl alcohol, lauryl alcohol and tetracosanol. Preferred alcohols are those of 1-6 carbons.

In the practice of the present invention toform alkoxysilanes, the mole ratio of oxime compound to silicon halide is at least n:1 and is preferably between n-1 and about 1.2 n:1. In cases wherein n is 3, this translates into a mole ratio between 3:1 and about 3.6:1.

In the practice of the present invention to form alkoxysilanes, the mole ratio of alcohol to silicon halide is at least n:1 and is preferably between n:1 and about 2n:1. Excesses of alcohol above the stoichiometric ratio (n:1) are not deleterious, and may in fact promote the desired alcohol reaction and suppress the undesired oxime reaction. Since the excess alcohol must be recycled to avoid being wasted, however, large excesses are not preferred.

When the oxime is in the preferred range of n:1 to about 1.2n:1, excesses of alcohol need not be large; and high yields of the desired product are obtained at 1.2n:1 or 1.2n:1 alcohol:silicon halide, with little increase in yields with still more alcohol.

In the practice of the present invention to produce oximinoalkoxysilane, the alcohol:silicon halide ratio (m) should be less than n:1 (to avoid producing mainly alkoxysilane). Thus if n is 3, m should be less than 3, with a preferred overall ratio being between 0.5 and 2.5. Thus, if the desired primary product is oximinodialkoxysilane, a value of m of about 2 is most preferred. If the desired primary product is dioximinomonoalkoxysilane, a value of m of about 1 is preferred. Ratios between 1 and 2 will produce these two as primary products. Ratios below 1 will produce dioximinomonoalkoxysilane and trioximinosilane as primary products; ratio above 2 will produce oximinodialkoxysilane and trialkoxysilanes as primary products. Similar preferred ratios are m as 0.5–1.5 when n is 2 and m as 0.5–3.5 when n is 4. Sufficient oxime should be present to complete the reactant stoichmetrics and HX neutralization, i.e. at least $(2n-m):1$.

Either the reaction may be done with neat reactants or in the presence of a solvent. It has been found that an inert hydrocarbon solvent such as hexane, petroleum ether, toluene, or other similar low-boiling materials may be advantageously used in order to lower the viscosity of the reaction mixture and to lower both the viscosity and the density of the product organosilane-containing phase so as to facilitate the separation of the organosilane products from the oxime hydrohalide, which may be either a solid or a heavier liquid. Excess alcohol may, in some cases, also serve these functions, provided that the alcohol does not hinder phase separation. Under such circumstances, the proportion of solvent to various reactants is not critical, with greater amounts of solvent acting to increase the ease of separation, but requiring additional evaporation or distillation to remove the solvent from the product after separation of the product from oxime hydrohalide by-product. For any particular system, the amount of solvent preferably used can be easily determined; and in the system of methyltrichlorosilane reacted with aliphatic alcohols of 1-6 carbons and methyl ethyl ketone oxime, a suitable ratio of solvent to methyltrichlorosilane is between about 1:1 and 2:1 by weight.

The temperature at which the reaction occurs is not critical, with the reaction occurring reasonably rapidly at room temperature or below, and with increasing speed but with some increase in formation of color bodies as the temperature increases. While a temmperature range from about 0° C. to about 100° C. is generally suitable, it is preferred, at least in the case of the reaction between methyltrichlorosilane, aliphatic alcohols of 1-6 carbons and methyl ethyl ketone oxime, to operate between about 20° C. and about 70° C. Because the reaction is exothermic, a temperature at the higher end of this range can normally be achieved by introducing the reactants at room temperature and, without extensive heat exchange, allowing the reaction mixture to heat up to a temperature of 30° to 60° C. The time of the reaction is also not critical since the reaction is virtually instantaneous with reaction times (in the case of batch processes) and residence times (in the case of continuous processes) generally being in the range of 5 minutes to 5 hours, and especially 30 minutes to 2 hours. It will be appreciated that a suitable reaction time can be determined by routine experimentation for any particular set of reactants, solvent, temperature and other operating conditions.

Once the reaction is completed, the product, the by-product oxime hydrohalide, the solvent and any unreacted oxime compound will generally separate into two phases which are either two liquid phases or a liquid phase and a solid phase at room temperature or above. The first or organic phase (which is usually the top phase) will contain essentially all the solvent, essentially all of the product organosilane, most of the unreacted oxime compound, most of the unreacted alcohol and only minor amounts of the by-product oxime hydrohalide. The second phase, which may be either a liquid (generally the bottom phase) or a solid, will contain the by-product oxime hydrohalide, with small or trace amounts of solvent, product oximinosilane, unreacted alcohol and unreacted oxime compound. Unreacted alcohol will normally only be present when the alcohol:silicon halide ratio was n:1 or above, since lesser amounts of alcohol would have been consumed in the reaction. The phases may be separated by any conventional technique, such as by decantation, filtration, centrifugation or other conventional techniques for separating solids from liquids or for separating two liquids of different densities. In general, relatively little time is required for the two phases to separate in essentially clean fashion.

Once the phases are separated, the product is recovered from the organic phase. One suitable method of purifying the product, especially of any by-product oxime hydrohalide, is to add to this organic phase a dry basic compound, which is preferably ammonia gas, so as to neutralize any oxime hydrohalide and generate inorganic halides (e.g. ammonium chloride) which forms an insoluble precipitate and free oxime compound. The solid inorganic halide is then removed (e.g. by filtration or centrifugation), while the solvent, any unreacted alcohol, any unreacted oxime compound and any oxime compound generated by the dry base are removed from the organic phase by flash evaporation, distillation or other similar technique which takes advantage of the relatively low boiling point of both the solvent and the oxime compound (and the alcohol) relative to the product organosilane. It is preferred that this evaporation be conducted at subatmospheric pressures, e.g. below 10 kPa, so as to minimize the temperature to which the product organosilane is exposed. Thereafter, after an optional filtration to remove any solids which may have formed or accumulated during the evaporation step, the product is ready for use. It will be appreciated that, depending upon what R, R', R'', R''', m and n are, the products can be useful in a variety of applications, and especially as room temperature vulcanizing or curing agents for silicones. It is not required to distill the product organosilanes as an overhead from any feed, but rather through the combination of filtration and evaporation of solvent, alcohol and oxime compound, a relatively pure alkoxysilane or oximinoalkoxysilane (or mixtures therebetween) may be produced.

In the separation of the reaction mixture, a second phase is formed containing principally oxime hydrohalide by-product. It is highly desirable to recover this material in useful form either for recycle to the reaction or otherwise. This material, after whatever purification may be required, may be used for the production of hydroxylamine salts, preferably in a manner of U.S. patent application Ser. No. 295,347, filed Aug. 24, 1981 of Bonfield et al. If, however, it is desired to regenerate oxime compound from this oxime hydrohalide, the preferred method is to mix this second phase with a base, so as to generate a salt (preferably an inorganic salt) and a free oxime compound. One contemplated method for conducting this neutralization is to add a dry base, and especially ammonia gas, to the second phase until a moderate pH, (e.g. pH 7) is achieved. Under these conditions large amounts of ammonium chloride or other ammonium halide will form as a precipitate in the oxime compound. By filtration or otherwise, the ammonium salt may be removed; and a dry oxime compound is then left, which may be recycled to the main reaction with halosilane. It is desirable in conducting such a neutralization with ammonia to thoroughly agitate the slurry as it forms so as to neutralize as much of the oxime hydrohalide as possible. It will be appreciated, however, that any oxime hydrohalide remaining in the oxime compound would be recycled and be relatively inert in the reaction mixture. Any alcohol present in this second phase would also be recycled.

An alternate method for neutralizing the oxime hydrohalide is to add an aqueous base solution such as aqueous ammonium hydroxide, aqueous sodium hydroxide, aqueous potassium hydroxide or the like so as to form an aqueous salt solution, which phase separates from an oxime compound. It is desirable in such a neutralization process to either use aqueous base of proper concentration, or to have a separate feed of water in proper ratio, to enable the mixture after neutralization to separate and form a saturated salt solution at the temperature involved (e.g. 25 percent sodium chloride at room temperature). The second layer would contain the oxime compound (e.g. methyl ethyl ketone oxime); and the solubility of the oxime compound in the saturated aqueous phase would then be minimized.

While neutralization with aqueous base is a generally easier procedure to follow, because of the ease of mixing, lower viscosity, and absence of solids, it has the disadvantage that it produces an oxime compound containing some dissolved water. Depending upon the use of which the oxime compound is to be put, the water may be removed by passage through a drying agent, distillation, azeotropic distillation or other techniques. If the intention is to recycle the oxime compound to the reaction with halosilane, it is desirable to remove the water from the oxime compound first, preferably down to levels of less than 1000 ppm.

The FIGURE illustrates a preferred embodiment of the process of the invention wherein reactor 10 is equipped with agitation and covered with an inert atmosphere (e.g. nitrogen) to assure reasonably anhydrous conditions. A solvent such as petroleum ether or hexane is fed in stream 11 to reactor 10. An oxime such as methyl ethyl ketone oxime (MEKO) and an alcohol such as isopropanol are fed in stream 12 to reactor 10. A halosilane (HS) such as methyltrichlorosilane (MTCS) is fed in stream 13 to reactor 10. All three streams should be essentially water-free (e.g. less than 1000 ppm water). The ratios of the three reactants may be, for example, those set forth in cases 1–11 below.

| Case | Silicon Chloride | n | Alcohol:HS | Oxime:HS |
|---|---|---|---|---|
| 1 | MTCS | 3 | 3 | 3 |
| 2 | MTCS | 3 | 4 | 3 |
| 3 | MTCS | 3 | 5 | 4 |
| 4 | MTCS | 3 | 2 | 4.5 |
| 5 | MTCS | 3 | 1 | 5 |
| 6 | DMDCS | 2 | 2 | 2 |
| 7 | DMDCS | 2 | 1 | 3 |
| 8 | DMDCS | 2 | 1 | 4 |
| 9 | STC | 4 | 4 | 4 |
| 10 | STC | 4 | 3 | 5 |
| 11 | TMCS | 1 | 1 | 1 |

The above cases, in which MTCS is methyltrichlorosilane (i.e. $n=3$), DMDCS (i.e. $n=2$), STC is silicon tetrachloride (i.e. $n=4$) and TMCS is trimethylchlorosilane (i.e. $n=1$) illustrate various stoichiometrics contemplated.

The major product is alkoxysilane in cases 1–3, 6, 9 and 11 where the molar ratio of alcohol to halosilane is at least 1. Thus, cases 1–3 are illustrated by the following reaction:

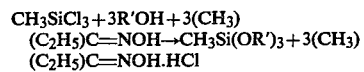

The major product is alkoxyoximinosilane where that ratio is less than 1. Thus, case 4 is illustrated by the following reaction (which will occur in competition with reaction leading to products with more or less alkoxy groups in the product):

CH₃SiCl₃+2R'OH+4(CH₃)
(C₂H₅)C=NOH→CH₃Si(OR')₂[(CH₃)
(C₂H₅)C=NO]+3(CH₃)(C₂H₅)C=NOH.HCl

Cases 2 and 3 illustrate the fact that larger amounts of alcohol may be present (in which case they will be recycled in the system of the FIGURE in stream 25). It is not preferred to use excess oxime without excess alcohol (i.e. 1:3:4 for MTCS) since the proportion of alkoxyoximnosilanes in what is intended to be alkoxysilane will increase. If it is desired to produce the mixed product, then it is preferred to cut down in the alcohol as in cases 4 and 5. Cases 6-8 indicate that, when n=2, a 2:1 (or higher) alcohol-silicon halide ratio is used to produce alkoxysilane, but a lower ratio (e.g. 1:1) is used to produce alkoxyoximinosilane. Cases 9-10 illustrate producing the two products when n=4. In n=1 (case 11) only one product can be produced.

Reactor 10 may be operated in batch, semi-continuous or continuous fashion with a residence time of about 0.5-2 hours. In batch operation an initially empty reactor 10 is charged with all three feeds and the reaction mixture is agitated for the desired period. Because of the reaction heat generated, some cooling may be applied by indirect cooling of the vessel or bleeding off solvent vapor, so as to limit the temperature to about 30°-60° C. at maximum. After the reaction period, reaction mixture is removed from reactor 10 in stream 14 to separation vessel 15.

In continuous operation, as reaction mixture is removed through stream 14, additional solvent, MEKO, alcohol, and MCS are added in approximately the same proportions as the initial charge, with the feed rates of streams 11, 12, and 13 matching the withdrawal rate in stream 14 (which may be an overflow) and with an average residence time at the desired 1-3 hour level.

Various combinations of batch and continuous operation will be apparent from the above to one skilled in the art, and the present invention is not limited to any particular form.

In separation vessel 15, a phase 16 consisting essentially of product organosilanes [e.g. methyl tris(isopropoxy)silane or mixtures including methyl diisopropoxy (methyl ethyl ketoximo) silane] and solvent will separate quickly and cleanly from a phase 17 consisting essentially of oxime hydrohalide (e.g. methyl ethyl ketone oxime hydrochloride or MEKOHC). Since MEKOHC is a liquid at room temperature, phase 17 is illustrated in the FIGURE as a liquid phase heavier than phase 16. For other oxime hydrohalide by-products (e.g. acetone oxime hydrochloride or cyclohexanone oxime hydrochloride), phase 17 is a solid such that separation vessel 15 is a centrifuge, filtration system or other similar liquid/solid separation device. Phases 16 and 17 are removed from vessel 15 continuously or intermittently and further treated as described below. A representative composition for phase 16 is over 40% organosilanes, about 40% solvent, under 2% MEKOHC, under 2% MEKO and minor amounts of alcohol, various by-products such as dimers and trimers of product organosilanes. A representative composition for phase 17 is over 95% MEDOHC, under 2% solvent, under 2% organosilanes, under 2% MEKO and minor amounts of alcohols.

Phase 16 is removed from separation vessel 15 to treatment vessel 18, equipped with agitation, where it is treated with dry ammonia gas fed in strem 19 in an amount sufficient to convert the MEKOHC to MEKO and ammonium chloride. Residence times in treatment vessel 18 of only a few minutes are required, but longer times may be used. The resultant thin slurry is withdrawn from treatment vessel 18 in stream 20 to filtration device 21 where the solid ammonium chloride is removed from the liquid. Periodically, the crude solid ammonium chloride is removed from filtration device 21 as shown by stream 22 for disposal or separation into organic and inorganic materials. A representative composition of the clarified stream 23 downstream of filtration device 21 is over 40% product organosilanes, about 40% solvent, under 0.01% MEKOHC, 3-4% MEKO and minor amounts of alcohol and dimers and trimers of the product organosilanes.

The clarified stream 23 is fed to vacuum stripper 24 where it is separated at subatmospheric pressure into a vapor stream 25 containing essentially all of the solvent, MEKO and alcohol, and a liquid bottom stream 26 containing the purified organosilane product. Stream 26 may be again filtered to remove any solids that form upon solvent evaporation (e.g. precipitated dimers and trimers) or may be used as taken from stripper 24. When the boiling point of the solvent (hexane=69° C. at 101 kPa) and MEKO (152° C. at 101 kPa) is significantly lower than the product (some products have boiling points over 150° C. at 101 kPa), a single plate is sufficient for stripper 24. Stripper 24 preferably operates under vacuum. If such differences are not present, more plates are required, and the product may be taken as an overhead fraction.

Phase 17 in separation vessel 15 (containing mainly MEKOHC) is fed continuously or intermittently to neutralization vessel 30 equipped with agitation. Aqueous base (e.g. 17% NaOH) is fed to vessel 30 in stream 31 in proportions producing in vessel 30 a suspension of an aqueous phase containing saturated inorganic salt (e.g. NaCl) and most of the alcohol present in phase 17 and an organic phase consisting of oxime compound (MEKO). This slurry is fed in stream 32 continuously or intermittently to a separation vessel 33 where it quickly and easily separates into oxime phase 34 and aqueous salt phase 35, both of which are removed. Aqueous phase 35 is cleared of residual organics (e.g. alcohols) in a conventional fashion and disposed of. Oxime phase 34, containing some water, may be purified in conventional fashion for use in a variety of processes requiring dry oxime (e.g. for recycle to stream 12) or used in wet form in other processes (e.g. for the production of hydroxylammonium chloride).

The present invention is illustrated by the following examples which, though conducted on a laboratory scale, are easily transferable to processes such as the one illustrated in the FIGURE.

EXAMPLE 1

Reaction of MTCS:Ethanol:MEKO at 1:3:3

In a 500 mL. 3-necked flask fitted with a thermometer, reflux condenser with drying tube, and a dropping funnel was placed a solution of methyl ethyl ketoxime (26.5 g.) (0.3 mol.) and absolute ethanol (14.5 g.) (0.3 mol.) in anhydrous ethyl ether (200 g.). The solution was stirred using a magnetic stirring bar with cooling in an ice-water bath. Maintaining the temperature between 10° and 20° C., methyl trichlorosilane (15 g.) (0.1 mol.) was added slowly and immediately a two-phase system was produced. After stirring for 10 minutes at ambient temperature, the reaction mixture was carefully transferred to a separatory funnel and the two phases collected separately.

The top phase (219 g.) was treated with ammonia gas when a fine precipitate of ammonium chloride separated out. This was filtered off and the clear filtrate, on removal of ether, gave a colorless liquid (19 g.). Analysis of this colorless liquid by gas chromatography showed that it was 91% pure methyl triethoxysilane containing small amounts of methyl diethoxy (methyl ethyl ketoximo) silane (4.8%) and methyl bis-(methyl ethyl ketoximo) ethoxysilane (1.4%). No methyl tris(-methyl ethyl ketoximo) silane was detected. The identity of the product as confirmed by GC-mass spec.

The heavy bottom phase (37 g.) was virtually pure methylethyl ketoxime hydrochloride, which was carefully neutralized with aqueous NaOH to recover the oxime as a separate phase.

EXAMPLE 2

Reaction of MTCS:Isobutanol-MEKO at 1:3:3

The same apparatus as in Example 1 was used and methyl trichlorosilane (15.4 g.) (0.1 mol.) was added with cooling and stirring to the solution of methyl ethyl ketoxime (28.3 g.) (0.32 mol.), isobutanol (23.6 g.) (0.32 mol.) in hexane (120 g.). The temperature reached a maximum of 35° C. during the addition. At the completion of addition the two-phase mixture was stirred at ambient temeprature for 30 minutes more. The phases were separated and the top phase (145.3 g.) was treated with ammonia gas. The precipitated amonium chloride was filtered off and the clear filtrate stripped of the solvent and the colorless liquid collected (27.2 g.). Gas chromatographic analysis of this mobile liquid showed that it contained primarily methyl tri-isobutoxysilane (73.8%) with methyl di-isobutoxy (methyl ethyl ketoximo) silane (19.4%) and methyl bis-(methyl ethyl ketoximo)isobutoxysilane (0.6%) as the other significant components. The product distilled at 85°-90° C. at 3 mm Hg.

The identities of these compounds were confirmed by GC mass spec. analysis.

The bottom phase (39.8 g.) of methyl ethyl ketoximo hydrochloride was neutralized with aqueous sodium hydroxide to recover the ketoxime.

EXAMPLE 3

Reaction of MTCS:Isobutanol:MEKO at 1:4:3

The same apparatus as in Example 1 was used, and the same procedure was followed as in Example 2. The only significant difference was in the amount of the reagents: isobutanol (35 g.) (0.47 mol.), methyl ethyl ketoxime (28 g.) (0.32 mol.), methyl trichloro silance (15 g.) (0.1 mol.), hexane (200 g.).

The two phases were separated in a separatory funnel and the clear top phase (233.8 g.) was treated with ammonia gas. After filtering off ammonium chloride the clear filtrate was stripped of hexane, and excess of isobutanol and a colorless mobile liquid collected (26.5 g.) Gas chromatographic analysis of this liquid showed that it was 94.1% pure methyl tri isobutoxy silane with only a small amount (4.6%) of methyl di isobutoxy (methyl ethyl ketoximo) silane as the significant impurity.

The bottom phase (43.7 g.) of methyl ethyl ketoxime hydrochloride was worked up in the usual manner with aqueous NaOH to recover methyl ethyl ketoxime.

EXAMPLE 4

Reaction of MTCS:Isobutanol:MEKO at 1:2:4

In a 500 mL. 3-necked flask fitted with thermometer, dropping funnel and reflux condenser fitted with drying tube was placed a solution of methyl ethyl ketoxime (35 g.) (0.4 mol.) and isobutanol (14.8 g.) (0.2 mol.) in hexane (160 g.). This was stirred using a magnetic stirring bar and maintained cold (10°-20° C.) during which methyl trichlorosilane (15 g.) (0.1 mol.) was added dropwise. After the addition was complete, cooling was removed and stirring continued at ambient temeprature for 30 minutes more.

The two clear phases were separated using a separatory funnel. The top phase of hexane solution (186.7 g.) was treated with ammonia gas for one minute and the separated precipitate of ammonium chloride was removed by filtration. The clear filtrate was then stripped of the solvent under reduced pressure and a colorless mobile liquid collected (26.5 g.). Gas chromatographic analysis of the liquid showed that it contained primarily methyl di isobutoxy (methyl ethyl ketoximo) silane (73.3%). The other significant components were methyl tri isobutoxy silane (11.5%), methyl tris (methyl ethyl ketoximo) silane (6.2%) and methyl bis-(methyl ethyl ketoximo) isobutoxysilane (1.0%). The identity of these components were confirmed by GC mass spec. The major product distilled at 65-°70° C. at 0.9 mm. Hg.

The viscous bottom phase (37.9 g.) of methyl ethyl ketoxime hydrochloride was worked up with aqueous sodium hydroxide to recover the oxime.

EXAMPLE 5

Reaction of DMDCS:Isobutanol:MEKO at 1:1:3

The same apparatus as in Example 4 was used. Dimethyldichlorosilane (12.9 g.) (0.1 mol.) was slowly added with stirring and cooling to a solution of isobutanol (7.4 g.) (0.1 mol.) and methyl ethyl ketoxime (26.1 g.) (0.3 mol.) in hexane (200 g.). On completion of addition the mixture was stirred for one hour and the phases separated in a separatory funnel.

The top phase of hexane solution (219.2 g.) was treated with ammonia gas and the precipitated ammonium chloride separated by filtration. The clear and colorless filtrate was stripped of hexane and a mobile liquid (20 g.) was collected. Gas chromatographic analysis showed that it was dimethyl isobutoxy (methyl ethyl ketoximo) silane (75.2%) together with dimethyl diisobutoxy-silane (17.8%) and dimethyl bis-(methyl ethyl ketoximo) silane (7.0%) as minor components. GC mass spec analysis confirmed the identity of the product (B.P. 45°-50° C./0.7 mm. Hg.).

The bottom phase (26.4 g.) of methyl ethyl ketoxime hydrochloride was neutralized with aqueous sodium hydroxide as before to recover methyl ethyl ketoxime.

EXAMPLE 6

Reaction of VTCS:Ethanol:MEKO at 1:2:4

The same apparatus as in Example 5 was used, and vinyl trichlorosilane (16.2 g., 0.1 mol.) was added slowly with stirring and cooling to a solution of ethanol (9.2 g., 0.2 mol.) and methyl ethyl ketoxime (34.8 g., 0.4 mol.) in hexane (190 g.). After stirring at ambient temperature for 30 minutes more, the two phases were separated. The bottom phase of MEKO hydrochloride (39.3 g.) was neutralized with aqueous NaOH to recover MEKO.

The top phase of the hexane solution (209.8 g.) was neutralized with ammonia gas for 2 minutes and the small amount of NH4Cl formed separated by filtration. The clear filtrate was stripped of hexane under reduced pressure to obtain a colorless liquid (20 g.). Gas chromatographic analysis showed the liquid to be vinyl diethoxy (methyl ethyl ketoximo) silane (67.1%), vinyl triethoxysilane (24.5%) and vinyl ethoxy bis-(methyl ethyl ketoximo) silane (8.4%). Less than 1% of vinyl tris-(methyl ethyl ketoximo) silane was present.

The identity of all the compounds was established by GC-mass spec. analysis.

EXAMPLE 7

Reaction of MTCS:Isopropanol:MEKO at 1:2:4

In a 5 liter jacketed resin kettle fitted with overhead stirring, thermometer and dropping funnel was placed a solution of isopropanol (600 g., 10 mol.) methyl ethyl ketoxime (1740 g., 20 mol.) and hexane (2000 mL.). Cold water at +5° C. was circulated from a cooling bath through the jacket and methyltrichlorosilane (750 g., 5 mol.) was slowly added maintaining the temperature of the reaction mixture between 20°–25° C. Addition was completed in 45 minutes and with cooling water circulation stopped the mixture was stirred for an additional 15 minutes. The bottom phase of methyl ethyl ketoxime hydrochloride was run off the bottom of the kettle and collected (1940 g.) as a viscous liquid. This was neutralized with aqueous NaOH to recover the oxime.

The top phase (2400 g.) was treated with ammonia gas from a cylinder for 2 minutes with stirring and a thin precipitate of ammonium chloride was formed. The solid was filtered off and the clear filtrate was stripped of hexane at maximum temperature of 90° C. at 25 mm. Hg. to furnish a colorless mobile liquid (1198 g.). Gas chromatographic analysis showed that the liquid was primarily methyl diisopropoxy (methyl ethyl ketoximo) silane (62.6&) together with methyl triisopropoxysilane (19.2%) and methyl isopropoxy bis-(methyl ethyl ketoximo) silane (15.1%).

The structures of the compounds were confirmed by GC-mass spec. analysis.

We claim:

1. A method for the production of an alkoxysilane which comprises:
   (a) reacting a silicon halide of the formula $R_{4-n}SiX_n$, wherein n is an integer between 1 and 4, inclusive, and R is alkyl of 1–6 carbons, alkenyl of 2–6 carbons, cycloalkyl of 4–8 carbons, aryl, alkyl-substituted aryl, aralkyl or halosubstituted forms of any of these with an alcohol of the formula R'OH, with R' being alkyl of 1–24 carbons or aralkyl, in the presence of an oxime compound of the formula R"R'"C=NOH, with R" and R'" each being hydrogen or alkyl of 1–6 carbons or forming an unsubstituted, halosubstituted or alkylsubstituted cycloalkyl ring of 4–8 carbons, and X is Cl, Br or I; the molar ratio of alcohol to silicon halide being at least n:1 and the molar ratio of oxime to silicon halide being at least n:1; and
   (b) recovering the alkoxysilane of the formula $R_{4-n}Si(OR')_n$ as major product and the hydrohalide of said oxime as byproduct.

2. The method of claim 1 wherein R" and R'" are each alkyl of 1–3 carbons and X is Cl.

3. The method of claim 2 wherein R is methyl.

4. The method of claim 2 wherein R is vinyl.

5. The method of claim 2 wherein R is phenyl.

6. The method of claim 1 or 2 wherein R' is alkyl of 1–6 carbons.

7. The method of claim 1 or 2 wherein n is 3.

8. The method of claim 7 wherein said recovering step (b) comprises:
   (i) separating a product phase from a byproduct phase,
   (ii) reacting the product phase with sufficient dry base to convert any dissolved oxime hydrohalide to oxime, and
   (iii) distilling the oxime so produced from the product alkoxysilane.

9. The method of claim 1 or 2 wherein said recovery step (b) comprises:
   (i) separating a product phase from a byproduct phase,
   (ii) reacting the product phase with sufficient dry base to convert any dissolved oxime hydrohalide to oxime, and
   (iii) distilling the oxime so produced from the product alkoxysilane.

10. The method of claim 1 or 2 wherein the molar ratio of alcohol to silicon halide is between n:1 and about 2 n:1 and the molar ratio of oxime to silicon halide is between about n:1 and about 1.2 n:1.

11. A method for the production of alkoxyoximinosilanes which comprises:
   (a) reacting a silicon halide of the formula $R_{4-n}SiX_n$ where R is alkyl of 1–6 carbons, alkenyl of 2–6 carbons, cycloalkyl of 4–8 carbons, aryl, alkyl-substituted aryl, aralkyl or halosubstituted forms of any of these, and n is an integer of 2–4 with an alcohol of the formula R'OH, where R' is alkyl of 1–24 carbons or aralkyl, and an oxime of the formula R"R'"C=NOH, with R" and R'" each being hydrogen or alkyl of 1–6 carbons or forming an unsubstituted, halosubstituted or alkylsubstituted cycloalkyl ring of 4–8 carbons, and X is Cl, Br or I; the molar ratio of alcohol to silicon halide being m:1, wherein m is at least about 0.1 n and less than n, and the molar ratio of oxime to silicon halide being at least (2n−m):1; and
   (b) recovering a product comprising at least one alkoxyoximinosilane of the formula $R_{4-n}Si(OR')_p(ON=CR"R''')_{n-p}$ where p is an integer of 1–3, but is at least one less than n, and the hydrohalide of said oxime as byproduct.

12. The method of claim 11 wherein R" and R'" are each alkyl of 1–3 carbons and X is Cl.

13. The method of claim 12 wherein R is methyl.

14. The method of claim 12 wherein R is vinyl.

15. The method of claim 12 wherein R is phenyl.

16. The method of claim 11 or 12 wherein R' is alkyl of 1–6 carbons.

17. The method of claim 11 or 12 wherein n is 3.

18. The method of claim 17 wherein said recovering step (b) comprises:
   (i) separating a product phase from a byproduct phase, (ii) reacting the product phase with sufficient dry base to convert any dissolved oxime hydrohalide to oxime, and
(iii) distilling the oxime so produced from the product alkoxyoximinosilane.

19. The method of claim 11 or 12 wherein said recovery step (b) comprises:
(i) separating a product phase from a byproduct phase,
(ii) reacting the product phase with sufficient dry base to convert any dissolved oxime hydrohalide to oxime, and
(iii) distilling the oxime so produced from the product alkoxyoximinosilane.

20. The method of claim 11 or 12 wherein the molar ratio of alcohol to silicon halide is between 0.5:1 and $(n-0.5):1$ and the mole ratio of oxime to silicon halide is not more than 2n:1.

* * * * *